US009265472B2

(12) United States Patent
Kälvesten et al.

(10) Patent No.: US 9,265,472 B2
(45) Date of Patent: Feb. 23, 2016

(54) METHODS, SYSTEMS, SERVICES AND CIRCUITS FOR GENERATING RAPID PRELIMINARY REPORTS WITH BONE MINERAL DENSITY MEASUREMENTS AND/OR OSTEOPOROSIS RISK ASSESSMENTS

(75) Inventors: Johan Kälvesten, Linköping (SE); Jakob Algulin, Linköping (SE)

(73) Assignee: Sectra AB, Linkoping (SE)

( * ) Notice: Subject to any disclaimer, the term of this patent is extended or adjusted under 35 U.S.C. 154(b) by 283 days.

(21) Appl. No.: 13/316,671

(22) Filed: Dec. 12, 2011

(65) Prior Publication Data

US 2013/0150700 A1    Jun. 13, 2013

(51) Int. Cl.
*A61B 6/00* (2006.01)
*G06F 19/00* (2011.01)

(52) U.S. Cl.
CPC ............. *A61B 6/502* (2013.01); *A61B 6/505* (2013.01); *A61B 6/5217* (2013.01); *A61B 6/563* (2013.01); *G06F 19/3487* (2013.01)

(58) Field of Classification Search
CPC ...... A61B 6/502; A61B 6/505; A61B 6/5217; A61B 6/563; G06F 19/3487
USPC .................. 600/407, 425; 382/128
See application file for complete search history.

(56) References Cited

U.S. PATENT DOCUMENTS

| | | | |
|---|---|---|---|
| 6,246,745 B1 * | 6/2001 | Bi et al. ........................... | 378/54 |
| 6,763,257 B1 | 7/2004 | Rosholm et al. | |
| 6,904,123 B2 * | 6/2005 | Lang .............................. | 378/54 |
| 8,370,293 B2 * | 2/2013 | Iwase et al. ................... | 707/608 |
| 2002/0131625 A1 * | 9/2002 | Vining et al. ................. | 382/128 |
| 2005/0111711 A1 * | 5/2005 | Deaven et al. ................ | 382/128 |
| 2007/0237378 A1 * | 10/2007 | Reiner ........................... | 382/128 |

OTHER PUBLICATIONS

Nguyen et al., "Haematological validation of a computer-based bone marrow reporting system", J. Clin. Pathol., 1997, vol. 50, pp. 375-378.*
Bach-Mortensen et al., Digital X-Ray Radiogrammetry Identifies Women at Risk of Osteoporotic Fracture: Results from a Prospective Study, Calcified Tissue International, 2006, pp. 1-6, vol. 79.
Black et al., A Normative Reference Database Study for Pronosco X-posure System™, Journal of clinical Densitometry, 2001, pp. 5-12, vol. 4, Issue 1, Abstract Only.
Boonen et al., Identifying postmenopausal women with osteoporosis by calcaneal ultrasound, metacarpal digital X-ray radiogrammetry and phalangeal radiographic absorptiometry: a comparative study, Osteoporosis International, Published online: Jun. 10, 2004, 17 pages.

(Continued)

*Primary Examiner* — Katherine Fernandez
(74) *Attorney, Agent, or Firm* — Myers Bigel & Sibley, P.A.

(57) ABSTRACT

Methods, systems, services (Internet), computer programs and circuits provide rapid bone mineral density (BMD) measurements and/or osteoporosis information using an automated image analysis circuit that evaluates a hand X-ray of a patient from an X-ray device to generate a reliable bone density evaluation within about 15 minutes, typically within about 5 minutes with receipt of a hand X-ray, and more typically substantially instantaneous and under 1 minute. The automated image analysis circuit can reside on a remote preliminary review server.

12 Claims, 11 Drawing Sheets

(56) References Cited

OTHER PUBLICATIONS

Bouxsein et al., Digital X-ray Radiogrammetry Predicts Hip, Wrist and Vertebral Fracture Risk in Elderly Women: A Prospective Analysis from the Study of Osteoporotic Fractures, Osteoporosis International, 2002, pp. 358-365, vol. 13.

Cootes et al., Active Shape Models—Their Training and Application, Computer Vision and Image Understanding, Jan. 1995, pp. 38-59, vol. 61, No. 1.

Dhainaut et al., The Ability of Hand Digital X-Ray Radiogrammetry to Identify Middle-Aged and Elderly Women with Reduced Bone Density, as Assessed by Femoral Neck Dual-Energy X-Ray Absorptiometry, Journal of Clinical Densitometry, Oct. 2010, pp. 418-425, vol. 13, Issue 4, Abstract only.

Early Prognosis for Osteoporosis, http://www.sectra.com/medical/womens_health/solutions/onescreen.com, Date unknown, printed from the internet Oct. 18, 2011.

Edwards et al., Interpreting Face Images using Active Appearance Models, Proceeding of the International Conference on Face and Gesture Recognition, 1998, pp. 300-305.

Lowe, David G., Object Recognition from Local Scale-Invariant Features, The Proceedings of the Seventh IEEE International Conference on Computer Vision, 1999, pp. 1150-1157, vol. 2.

Reed et al., The use of digital X-ray radiogrammetry and peripheral dual energy X-ray absorptiometry in patients attending fracture clinic after distal forearm fracture, Bone, Apr. 2004, pp. 716-719, vol. 34, Issue 4, Abstract Only.

Rosholm et al., Estimation of Bone Mineral Density by Digital X-ray Radiogrammetry: Theoretical Background and Clinical Testing, Osteoporosis International, 2001, pp. 961-969, vol. 12.

Ashford et al., Digital X-Ray Radiogrammetry Predicts Hip Fracture in Elderly Women, Journal of Bone and Mineral Research, 2001, vol. 16, Supplement 1, 1 page, Abstract.

Bach-Mortensen et al., Prediction of Osteoporotic Fracture by Digital X-ray Radiogrammetry and DXA. A Case-control Study of Three Different Fracture Types, Journal of Bone and Mineral Research, 2001, vol. 16, Supplement 1, 1 page, Abstract.

Haigh et al., Digital X-ray Radiogrammetry Indices are Sensitive to Clodronate Treatment in Women With Osteoporosis, ASBMR, 2002, 1 page, Abstract.

Shepherd et al., Digital X-ray Radiogrammetry in Assessing Age-related Loss, Fracture Discrimination, and Diagnostic Classification, Journal of Bone and Mineral Research, 2001, vol. 16, Supplement 1, 1 page, Abstract.

Vasireddy et al., Digital X-ray Radiogrammetry Indices, Particularly MCI, Can Predict Vertebral Fracture Risk in Osteoporotic Women, ASBMR, 2002, 1 page, Abstract.

* cited by examiner

NO PRELIMINARY REPORT

FAILURE MESSAGE

METHODS, SYSTEMS, SERVICES AND CIRCUITS FOR GENERATING RAPID PRELIMINARY REPORTS WITH BONE MINERAL DENSITY MEASUREMENTS AND/OR OSTEOPOROSIS RISK ASSESSMENTS

BACKGROUND

Sectra OneScreen™ is a service that measures women's bone health (Bone Mineral Density, "BMD") using a single, standard X-ray image of the hand. This service is often used with mammography screenings using the mammography X-ray machine or in a workflow for distal radius fractures.

SUMMARY

Embodiments of the invention provide generate rapid preliminary patient reports with at least one of a BMD measurement or an osteoporosis risk evaluation that is carried out automatically using a defined image processing module.

The preliminary report can be generated substantially instantaneously once the X-ray is obtained, then rapidly transmitted to a user (typically a clinician, but also or alternatively, the patient). The rapid report can be generated while the patient is onsite at the medical facility.

The preliminary report may include a label, statement or header that identifies the report as preliminary and subject to change in a final report, once the X-ray or report is analyzed manually by an expert or specialist (e.g., a person trained in validating the BMD measurements).

The rapid automated analysis circuit can be configured to transmit only measurements or reports with risk assessments for patients where those measurements or evaluations are considered reliable.

Some embodiments are directed to a medical evaluation service that includes at least one preliminary review server in communication with a plurality of radiology sites via the Internet. The at least one preliminary review server can be in direct or indirect communication with a clinician workstation or imaging modality (e.g., for an indirect communication, via a PACS system). The at least one preliminary review server is configured to receive hand X-ray images with patient data, perform an automated rapid bone mineral density (BMD) evaluation using a respective hand X-ray, generate an associated preliminary report of the BMD evaluation, then electronically transmit the preliminary report back to at least one user substantially instantaneously from time of receipt of a hand X-ray at the preliminary review server.

The at least one preliminary review server can be configured to perform the automated rapid BMD evaluation using an image analysis model that evaluates at least one (typically a plurality of) middle metacarpal bone in the hand X-ray image to determine a BMD measurement. The at least one preliminary review server can be configured to determine whether the BMD measurement is reliable and to only send the preliminary report with the BMD measurement if it is considered reliable.

The at least one preliminary review server can be configured to perform the automated rapid BMD evaluation using an image analysis model that evaluates at least one (typically a plurality of) middle metacarpal bone in the hand X-ray image to determine a BMD measurement. The at least one preliminary review server can be configured to determine whether the BMD evaluation is reliable using a defined risk threshold and to only transmit the preliminary report with the BMD measurement if sources of error associated with the evaluation are below the defined risk threshold. If the BMD measurement is determined to be unreliable, a different preliminary report with no BMD measurement can be transmitted to the user.

The defined risk threshold can be based on electronically identified residual errors and/or image parameter irregularities associated with the BMD evaluation of the X-ray image. The preliminary report can include a color-coded graph with a patient's BMD measurement, a T-score and a Z-score. The preliminary report can be transmitted back to a user within less than one minute after receipt of the hand X-ray at the at least one preliminary review server.

The workstations at respective radiology sites can be in communication with an X-ray apparatus. The server can be configured to perform the evaluation and generate and transmit the preliminary report substantially instantaneously from a time of acquisition of a respective hand X-ray from the X-ray apparatus.

Other embodiments are directed to methods for providing rapid bone mineral density (BMD) measurements and/or osteoporosis information. The methods include: (a) obtaining a hand X-ray of a patient from an X-ray device; (b) electronically evaluating the hand X-ray to determine a BMD measurement using an automated image analysis circuit; (c) electronically generating a preliminary report based on the BMD measurement; and (d) electronically transmitting the preliminary report to at least one user. The preliminary report is transmitted within about 5 minutes or less from when the X-ray is obtained.

The method can also include electronically transmitting the obtained hand X-ray to a remote preliminary review server using a DICOM transmission format for the electronic evaluation. The electronic evaluation, preliminary report generation can all be carried out by the remote preliminary review server to transmit the preliminary report within about 15 minutes, typically in under 10 minutes, such as within about 7 minutes, about 6 minutes, about 5 minutes or even less such as within about 1 minute, with the preliminary report providing a reliable evaluation of BMD associated with risk of osteoporosis.

The method can include electronically determining whether the BMD evaluation is reliable, wherein the report is transmitted (with the evaluation) only if the determination finds the BMD evaluation to be reliable.

The method can include electronically determining whether there are residual errors and/or irregular image features to calculate a risk threshold for establishing whether data is reliable. The preliminary report with the BMD measurement is transmitted if the data is identified as reliable.

In some embodiments, if data from the evaluation is considered unreliable, the transmitting the preliminary report is carried out to transmit the preliminary report without a BMD measurement and/or with a message that notes no rapid evaluation can be carried out.

The method can include providing the respective hand X-ray of a patient to an expert for manual review after the transmitting the preliminary report to the user.

The method can optionally include transmitting a final report of a BMD evaluation to the at least one user after the transmitting the preliminary report. The final report validates the preliminary report at least 90% of the time.

The preliminary report can includes color-coded graph with a patient's BMD measurement, a T-score and a Z-score.

The method can include transmitting a final report of a BMD evaluation to the at least one user after the transmitting the preliminary report. The final report validates data in the preliminary report at least 90% of the time.

Still other embodiments are directed to rapid analysis and preliminary reporting systems for evaluating BMD (bone mineral density) for assessing a patient's risk of osteoporosis. The systems include: (a) a radiology workstation in communication with a display; (b) an X-ray device in communication with the workstation; and (c) a preliminary BMD report circuit with an automated rapid image analysis module. The preliminary report circuit is configured to analyze a hand X-ray taken from the X-ray device using an image analysis model that is applied to a plurality of middle metacarpal fingers in a respective hand X-ray undergoing analysis, then electronically transmit an associated BMD measurement with an osteoporosis risk report to a user. The circuit is configured to carry out the analysis, generate the preliminary report and transmit it to the user substantially instantaneously upon receipt of a respective hand X-ray from the radiology workstation or the X-ray device (which can optionally be a mammography X-ray device).

The system can include a remote expert workstation in communication with the preliminary report circuit and/or radiology workstation. The expert workstation is configured to allow an expert to review a respective hand X-ray and associated preliminary report and decide whether to validate or invalidate data reported in the preliminary report.

The remote workstation can be configured to transmit a final report to at least one user.

The preliminary report circuit can be held at least partially in a remote server. The radiology workstation or X-ray device can (directly or indirectly) transmit the hand X-ray images (with patient data) in DICOM format to the remote server via the Internet.

The preliminary review circuit can be configured to carry out the analysis, generate and transmit the preliminary report to the at least one user within about 30 seconds from receipt of a respective hand X-ray from the radiology workstation, radiology site and/or the X-ray device.

The preliminary review circuit can be configured to electronically determine whether the BMD measurement is reliable. The preliminary review circuit can be configured to transmit the preliminary report with the BMD measurement only if the BMD measurement is determined to be reliable.

The preliminary review circuit can be configured to electronically determine whether there are residual errors and/or irregular image features to calculate a risk threshold for establishing whether the BMD measurement is reliable. The preliminary review circuit can be configured to transmit the preliminary report with the BMD measurement only if the BMD measurement is determined to be reliable.

In some embodiments, if the BMD measurement is considered unreliable, the preliminary review circuit can be configured to transmit the preliminary report without a BMD measurement and/or with a message that notes no rapid evaluation can be carried out.

The preliminary report can include a color-coded graph with a patient's BMD measurement, a T-score and a Z-score.

The expert review site can validate the preliminary report at least 90% of the time.

Still other aspects are directed to computer program products for providing rapid preliminary bone mineral density (BMD) measurements. The computer program product includes a non-transitory computer readable storage medium having computer readable program code embodied in the medium. The computer-readable program code includes: (a) computer readable program code configured to receive a hand X-ray of a patient generated by an X-ray device; (b) computer readable program code configured to evaluate the hand X-ray to determine a BMD measurement using an automated image analysis module; (e) computer readable program code configured to generate a preliminary BMD evaluation report based on the BMD measurement; and (d) computer readable program code configured to transmit the preliminary BMD evaluation report to at least one user, wherein the report is transmitted to a user within about 15 minutes or less, such as about 5 minutes or less, or even about 1 minute or less, from a time of receipt of the hand X-ray.

The computer program code can include computer program code that receives the X-ray is associated with a remote preliminary review server that receives the X-ray images using a DICOM transmission format.

The computer program code can also include computer program code that determines whether the BMD measurement is reliable. The computer program code that is configured to transmit the preliminary report can be configured to transmit the preliminary report with the BMD measurement only if the BMD measurement is determined to be reliable.

The computer program product can include computer readable program code configured to determine whether there are residual errors and/or irregular image features to calculate a risk threshold for establishing whether data associated with the BMD evaluation report is reliable. The preliminary report with the BMD measurement can be transmitted only if the data is identified as reliable.

The computer program product can also include computer readable program code to generate a different preliminary report when the data is considered unreliable such that the preliminary report is transmitted without a BMD measurement and with a message that notes no rapid evaluation can be carried out.

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

DETAILED DESCRIPTION OF EMBODIMENTS OF THE INVENTION

Figure 1:
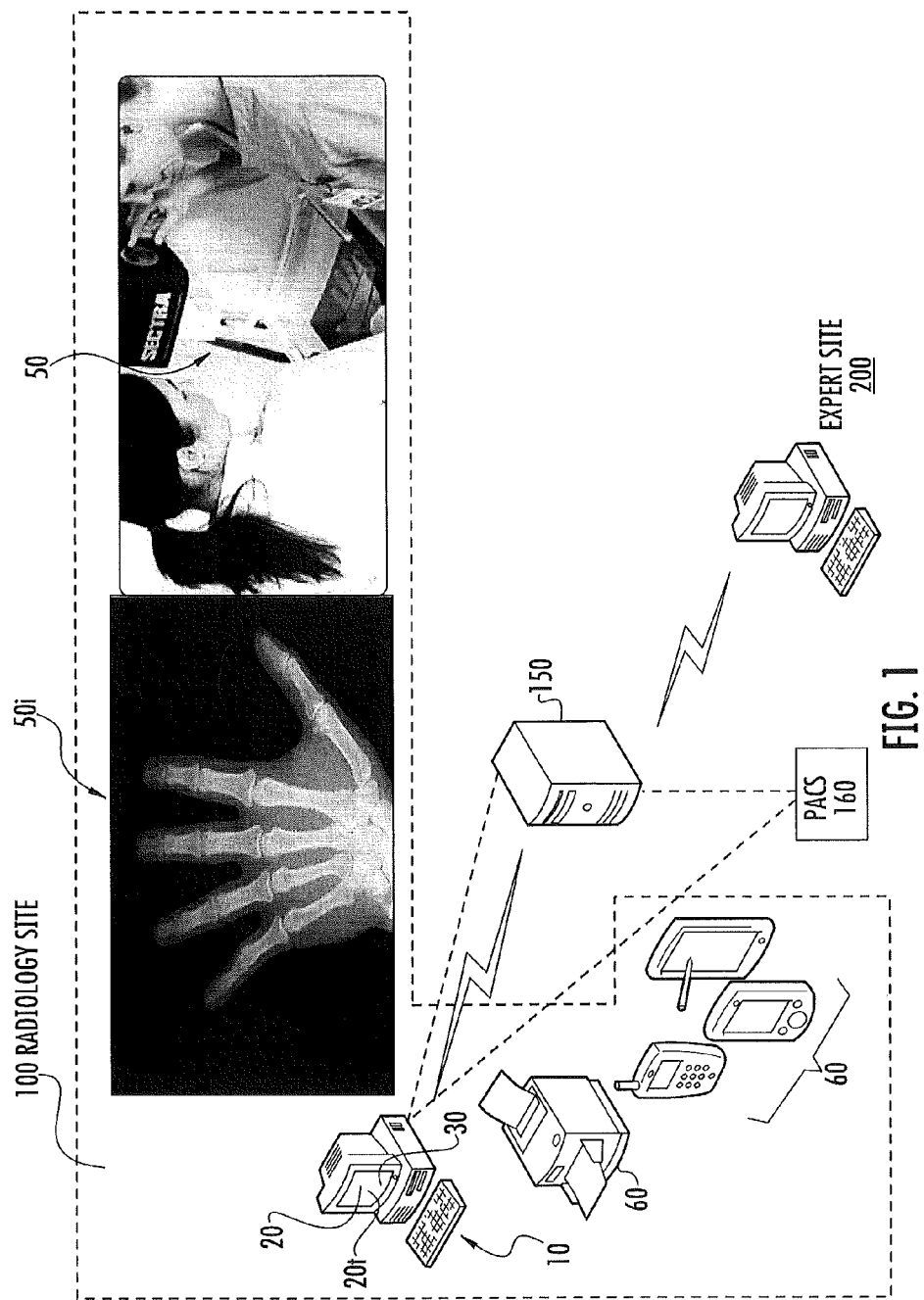
FIG. 1 is a schematic illustration of a rapid automated image analysis and preliminary reporting circuit according to some embodiments of the present invention.

The present invention will now be described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. It will be appreciated that although discussed with respect to a certain embodiment, features or operation of one embodiment can apply to others.

In the drawings, the thickness of lines, layers, features, components and/or regions may be exaggerated for clarity and broken lines (such as those shown in circuit or flow diagrams) illustrate optional features or operations, unless specified otherwise. In addition, the sequence of operations (or steps) is not limited to the order presented in the claims unless specifically indicated otherwise.

Generally stated, some embodiments of the invention are directed to providing reliable, rapid automated (using an image processing circuit) preliminary bone mineral density (BMD) measurement for osteoporosis risk evaluation or screening ("BMD/O"). The preliminary reports can be subsequently validated or invalidated by an expert to generate a "final" BMD/O report. The osteoporosis risk or screening can evaluate a patient's fracture risk associated with various parameters such as one or more of a BMD measurement, Z-score or T-score. A fracture risk typically depends on a population studied (for determining percentile ranks), thus patient data for the analysis can include, for example, one or more of age, gender, and ethnicity. Osteoporosis evaluation methods are well known with many associated publications. An example of a publication on this topic is: Textbook of Osteoporosis, John A. Kanis, Cambridge, Mass. Blackwell Science, 1996. The contents of this document are hereby incorporated by reference as if recited in full herein.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof, As used herein, the term "and/or" includes any and all combinations of one or more of the associated listed items. Like numbers refer to like elements throughout. In the figures, the thickness of certain lines, layers, components, elements or features may be exaggerated for clarity. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when a feature, such as a layer, region or substrate, is referred to as being "on" another feature or element, it can be directly on the other element or intervening elements may also be present. In contrast, when an element is referred to as being "directly on" another feature or element, there are no intervening elements present. It will also be understood that, when a feature or element is referred to as being "connected" or "coupled" to another feature or element, it can be directly connected to the other element or intervening elements may be present. In contrast, when a feature or element is referred to as being "directly connected" or "directly coupled" to another element, there are no intervening elements present. The phrase "in communication with" refers to direct and indirect communication, Although described or shown with respect to one embodiment, the features so described or shown can apply to other embodiments.

The term "circuit" refers to software embodiments or embodiments combining software and hardware aspects, features and/or components, including, for example, at least one processor and software associated therewith embedded therein and/or executable by and/or one or more Application Specific Integrated Circuits (ASICs), for programmatically directing and/or performing certain described actions, operations or method steps. The circuit can reside in one location or multiple locations, it may be integrated into one component or may be distributed, e.g., it may reside entirely in a workstation or single computer, partially in one workstation, cabinet, or computer, or totally in a remote location away from a local display at a workstation. If the latter, a local computer and/or processor can communicate over a LAN, WAN and/or internet to transmit patient X-rays for the automated rapid preliminary evaluation or for a remote manual evaluation at an expert site. Typically, the circuit includes a DICOM system that transmits the images from the X-ray apparatus and/or X-ray site to a remote server for rapid analysis.

Embodiments may be particularly suitable for use with digital X-rays.

The term "automatically" means that the operation can be substantially, and typically entirely, carried out without human or manual input, and is typically programmatically directed or carried out. The term "electronically" includes both wireless and wired connections between components.

The term "clinician" refers to a physician, radiologist or other personnel desiring to review medical data of a subject, which is typically a live human or animal patient. The term "expert" refers to a person trained in validating the BMD measurements. The term "user" refers to a person, or device associated with that person, that uses the claimed feature or item, such as an expert, clinician or patient.

The term "PACS" refers to PICTURE ARCHIVING AND COMMUNICATION SYSTEMS.

The term "substantially instantaneously" means that a respective image is electronically analyzed (typically via an image processing circuit at a remote server) and the associated preliminary BMD or BMD/O report is generated and electronically transmitted back to the imaging site, to a clinician site, and/or to a patient within a few minutes, typically within a few seconds, such as within 15 minutes, such as under about 10 minutes, including about 7 minutes or less, about 6 minutes or less, or about 5 minutes or less. In some embodiments, the analysis and transmission back is within about 5 minutes or less, such as within about 4 minutes, within about 3 minutes, within about 2 minutes, or within about 1 minute from receipt of the hand X-ray at the automated review circuit or from when the hand X-ray is obtained by an X-ray device. In some embodiments, the analysis and transmission can be carried out in about 1 minute or less, such as within about 45 seconds, within about 30 seconds or even within about 15 seconds or less (depending on bandwidth). The substantially instantaneous time frame can be measured from when the hand X-ray is obtained at an imaging site to when the report is received back at the imaging site (or at another designated site or user). The substantially instantaneous time frame can be measured from when the hand X-ray image is electronically received at a remote site (e.g., server) with relevant patient data, including age or date of birth and gender to when it is received back at the X-ray imaging site (or to another designated site or user).

The term "reliable" with reference to the preliminary report means that the BMD measurement and/or osteoporosis evaluation provided by the preliminary report is statistically valid at least 90% of the time such as above 90% of the time, including about 95% of the time or even at least about 99% of the time, such as about 99.8% of the time, e.g., that upon expert review no changes are made to the BMD measurement, the T-score or the Z-score.

The X-ray image can be electronically automatically transmitted using a DICOM system to a remote server for the automated image analysis. The X-ray transmission to the remote server can be triggered when a local user selects a "send" instruction or a "save" instruction, the latter indicating the X-ray is acceptable at the acquisition site.

Generally stated, osteoporosis, particularly in women, is a large and costly problem. Osteoporosis screening is one method that attempts to alleviate this problem. Recently, technology and workflow have been developed that allow efficient combination of mammography screening with osteoporosis screening. See, e.g., U.S. Pat. No. 6,763,257, the contents of which are hereby incorporated by reference as if recited in full herein.

In some markets, women are forced to wait for relatively lengthy periods in the clinic of the screening to receive the results of their mammography screening. It can be particularly desirable to provide an osteoporosis screening with BMD results before the person leaves the clinic. This can allow for a more prompt intervention and/or a more cost effective medical review, where osteoporosis risk is identified, as this can obviate a need for a return visit to a medical facility or doctor based on a later unfavorable risk report.

It is contemplated that in other markets, such as where a patient has a short radiology visit, potentially followed by some subsequent doctor follow-up, the rapid osteoporosis screening using X-ray image data can also be beneficial. The rapid preliminary BMD/O risk information (when reliable) may promote more compliant behavior to treat an identified risk via diet, medicinal, exercise or other therapeutic interventions or subsequent medical follow-up. The X-ray site may offer brochures on treatment options to inform a patient as to treatment choices and/or facilitate compliance or treatment to reduce the risk of bone fractures due to osteoporosis. Having this information available with presentation of a preliminary report (or while a patient waits for a mammogram) may be beneficial.

Turning now to FIG. 1, a radiology site 100 is in communication with an image analysis and preliminary report server 150. The radiology site 100 is also in communication with an expert site 200. The expert site 200 can be remote from the radiology site 100. The image analysis and preliminary report server 150 can be remote from both the radiology site 100 and the expert site 200. Alternatively, the image analysis and preliminary report server 150 can be onsite either the expert or radiology site 200, 100, respectively. The image analysis and preliminary report server 150 can be integrated into a single server or may be distributed into one or more servers or other circuits or databases at a single physical site or at spatially separate locations. Similarly, the image analysis circuit or module 124 held by the one or more servers 150, can be distributed into multiple processors or databases or integrated into one.

The server 150 may be embodied as a standalone server or may be contained as part of other computing infrastructures. The preliminary report server 150 may be embodied as one or more enterprise, application, personal, pervasive and/or embedded computer systems that may be standalone or interconnected by a public and/or private, real and/or virtual, wired and/or wireless network including the Internet, and may include various types of tangible, non-transitory computer-readable media. The server 150 may also communicate with the network via wired or wireless connections, and may include various types of tangible, non-transitory computer-readable media.

The server 150 can be provided using cloud computing which includes the provision of computational resources on demand via a computer network. The resources can be embodied as various infrastructure services (e.g. compute, storage, etc.) as well as applications, databases, file services, email, etc. In the traditional model of computing, both data and software are typically fully contained on the user's computer; in cloud computing, the user's computer may contain little software or data (perhaps an operating system and/or web browser), and may serve as little more than a display terminal for processes occurring on a network of external computers. A cloud computing service (or an aggregation of multiple cloud resources) may be generally referred to as the "Cloud". Cloud storage may include a model of networked computer data storage where data is stored on multiple virtual servers, rather than being hosted on one or more dedicated servers.

A plurality of the sites 100 can be in communication with the preliminary report server 150 and one or more expert sites 200. The server 150 can receive and analyze multiple hand X-ray images of respective patients from the different sites 100 at any one time. It is contemplated that the server 150 can generate the reports in a FIFO (first in first out) manner and such that multiple analyses and associated reports can be carried out and transmitted to one or more users in a rapid (e.g., substantially instantaneous) fashion.

The radiology site 100, image analysis and preliminary report server 150, and expert site 200 can communicate via a computer network, such as one or more of local area networks (LAN), wide area networks (WAN) and can include a private intranet and/or the public Internet (also known as the World Wide Web or "the web" or "the Internet"). The server 150 can include and/or be in communication with a module 124 that performs the rapid automated image analysis. Discussion of some examples of automated image analysis is provided below.

The radiology site 100 includes at least one workstation 10 with a display or screen 20. It is noted that the terms "display" and "screen" are used interchangeably. The display 20 can include a GUI 22 which employs a touch-input/touch-screen 20*t*. However, the display 20 and/or workstation 10 can employ other user interfaces (UI). The radiology site 100 also includes at least one X-ray device 50 configured to obtain a hand X-ray 50*i*. The device 50 is in communication with the workstation 10 and may be directly or indirectly in communication with the remote server 150. The X-ray device 50 may be a mammography X-ray device or another X-ray device capable of obtaining the hand X-ray.

The X-ray device 50 and/or workstation 10 can be in communication with a PACS system 160 (FIG. 1). The hand X-ray can be transmitted from the X-ray site 100 by any of the X-ray device 50, the workstation 10 and/or the PACS system 160 or any other suitable communication system.

The radiology site 100 can also include one or more report output devices 60, including a display 20 (onboard the workstation 10 or associated with another computer), a printer, a facsimile machine, and pervasive computer devices such as electronic notepads, smartphones, cell phones and the like. The preliminary report 200*p* (FIG. 5, 8A) can be delivered by email, facsimile, and/or directly to RIS (Radiology Information System), HIS (Hospital Information System) or PACS systems 160 (FIG. 1).

Figure 8A:
FIG. 8A is an example of a preliminary report according to some embodiments of the present invention.
Figure 8B:
FIG. 8B is an example of a final report according to some embodiments of the present invention.

The workstation 10 can include a software access module or gateway 30 that allows access to the server 150 for the preliminary report 200*p* (FIG. 8A). The BMD/O review then also typically requires that a manual review to validate or invalidate the earlier report (final report) 200*f* (FIG. 8B). The final report is based on review by a trained expert (human operator) that is typically performed of every BMD/O automated examination at the expert site 200. The purpose of the review is primarily to detect user error by X-ray technicians but in exceptional cases also failures by the image analysis software. Thus, the expert site 200 can include at least one workstation 210.

A hand X-ray image 50*i* can be electronically transmitted to the server 150 by means of the DICOM standard for image transfer. Preferably, the data transfer is encrypted and is done via the Internet using any appropriate firewalls to comply with industry or regulatory standards such as HIPAA. The term "HIPAA" refers to the United States laws defined by the Health Insurance Portability and Accountability Act. The patient data can include an accession number or identifier, gender, age and ethnicity.

The workstation 10 gateway or module 30 can allow a user to select the BMD/O evaluation in conjunction with another workflow, e.g., mammogram or distal radius fracture. This selection electronically automatically causes the both the preliminary report and the subsequent the final report to be generated. The local X-ray site 100 can forward the hand X-ray directly to the expert site 200 for review as well as the remote server 150 or may otherwise transmit the X-ray data to the remote expert site 200.

Figure 2:
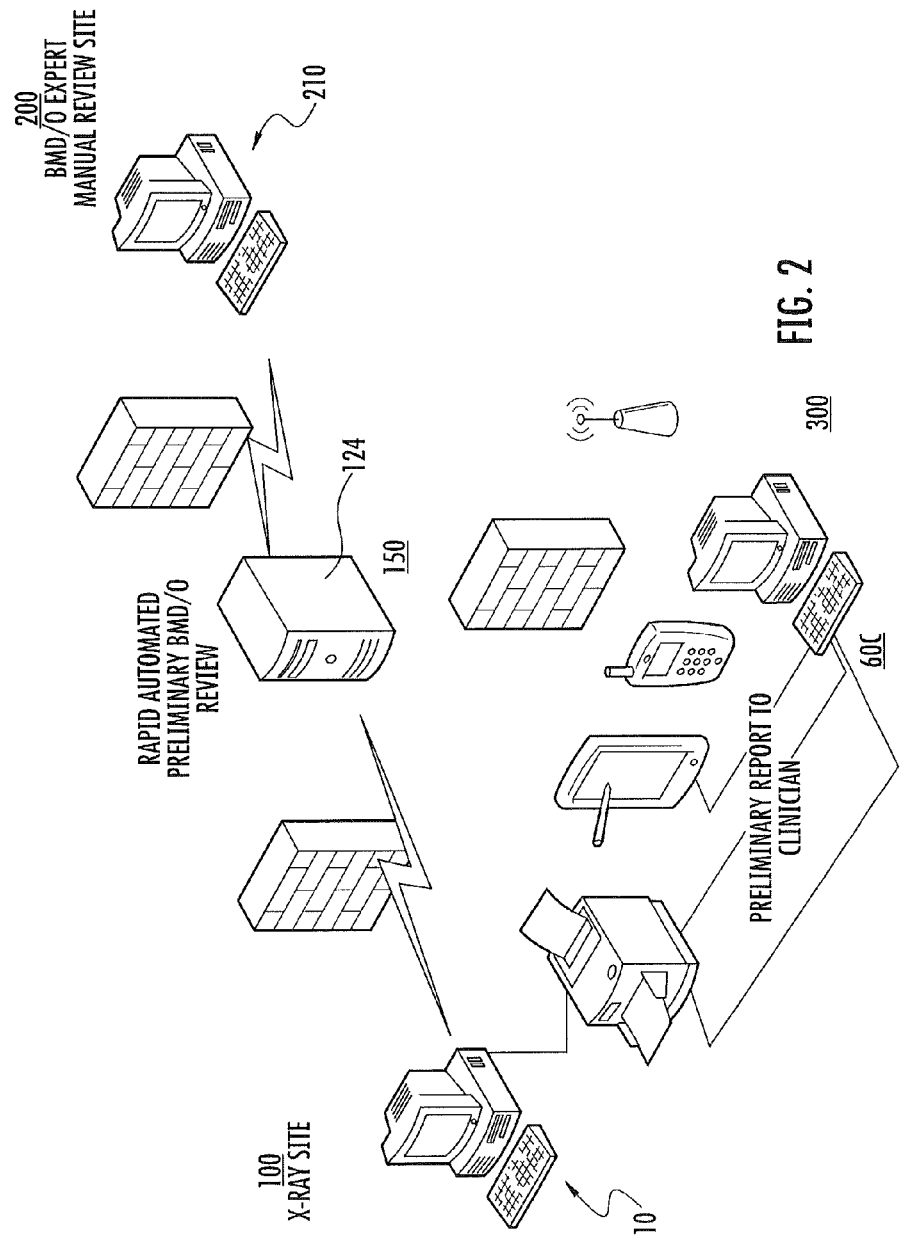
FIG. 2 is a schematic illustration of a rapid automated image analysis and preliminary reporting circuit according to some embodiments of the present invention.
Figure 3:
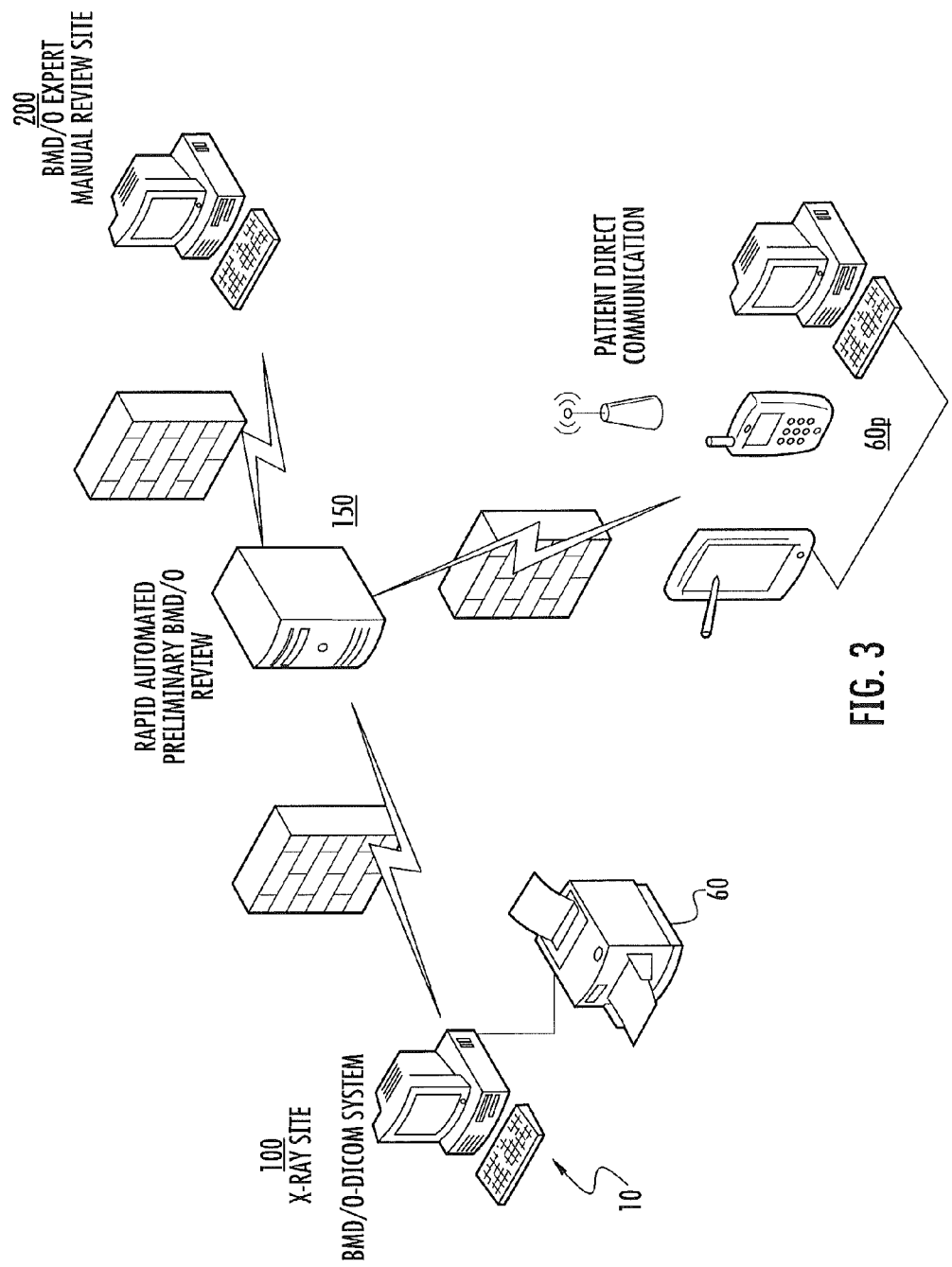
FIG. 3 is a schematic illustration of a rapid automated image analysis and preliminary reporting circuit according to some embodiments of the present invention.
Figure 4:
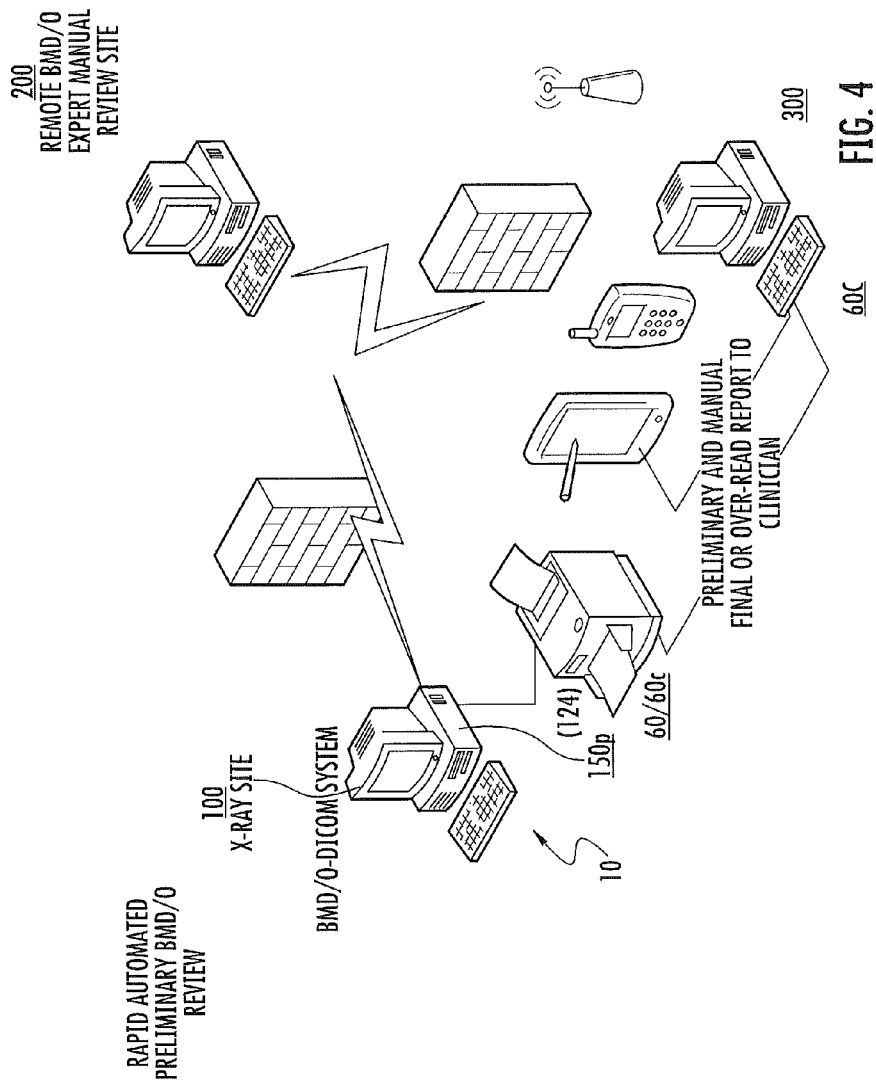
FIG. 4 is a schematic illustration of a rapid automated image analysis and preliminary reporting circuit according to some embodiments of the present invention.

FIGS. 2-4 illustrate exemplary systems that can generate the automated rapid BMD/O reports 200*p* (FIG. 8A). FIG. 2 illustrates that the preliminary report 200*p* can be sent to a clinician's office that is typically at a location 300 that is separate from the X-ray site (or X-ray room). That is, the clinician's office may be at the same clinic as the X-ray room. The report 200*p* can be transmitted as an electronic record to one or more output devices 60*c* including, for example, a computer, smartphone, electronic notepad, facsimile machine, printer and the like. The report 200*p* can also be transmitted to the X-ray site 100 and can be provided to a patient and/or placed in a database such as PACS for a patient historical record.

FIG. 3 illustrates that the preliminary report 200*p* can be sent directly to a patient using a patient's computer, electronic notepad, facsimile machine, cellular phone or smartphone. The report 200*p* can be sent as a copy of a one sheet formal report or as a text message "BMD/O risk assessment indicates there is or is not a risk of osteoporosis" and the message can indicate whether that risk is little, slight, high or low risk level for osteoporosis. The report 200*p* can be sent to more than one location including, for example, the X-ray site 100, clinic site 300 and to the patient.

FIG. 4 illustrates that that the image analysis processor 124 can be included in a clinic processor or server 150*p* and does not require the remote server 150. The local and/or remote preliminary review image analysis processor can optionally also or alternatively be used for an over-read. The over-read using the image analysis module 124 can be used to audit the reliability of other BMD assessments.

Figure 5:
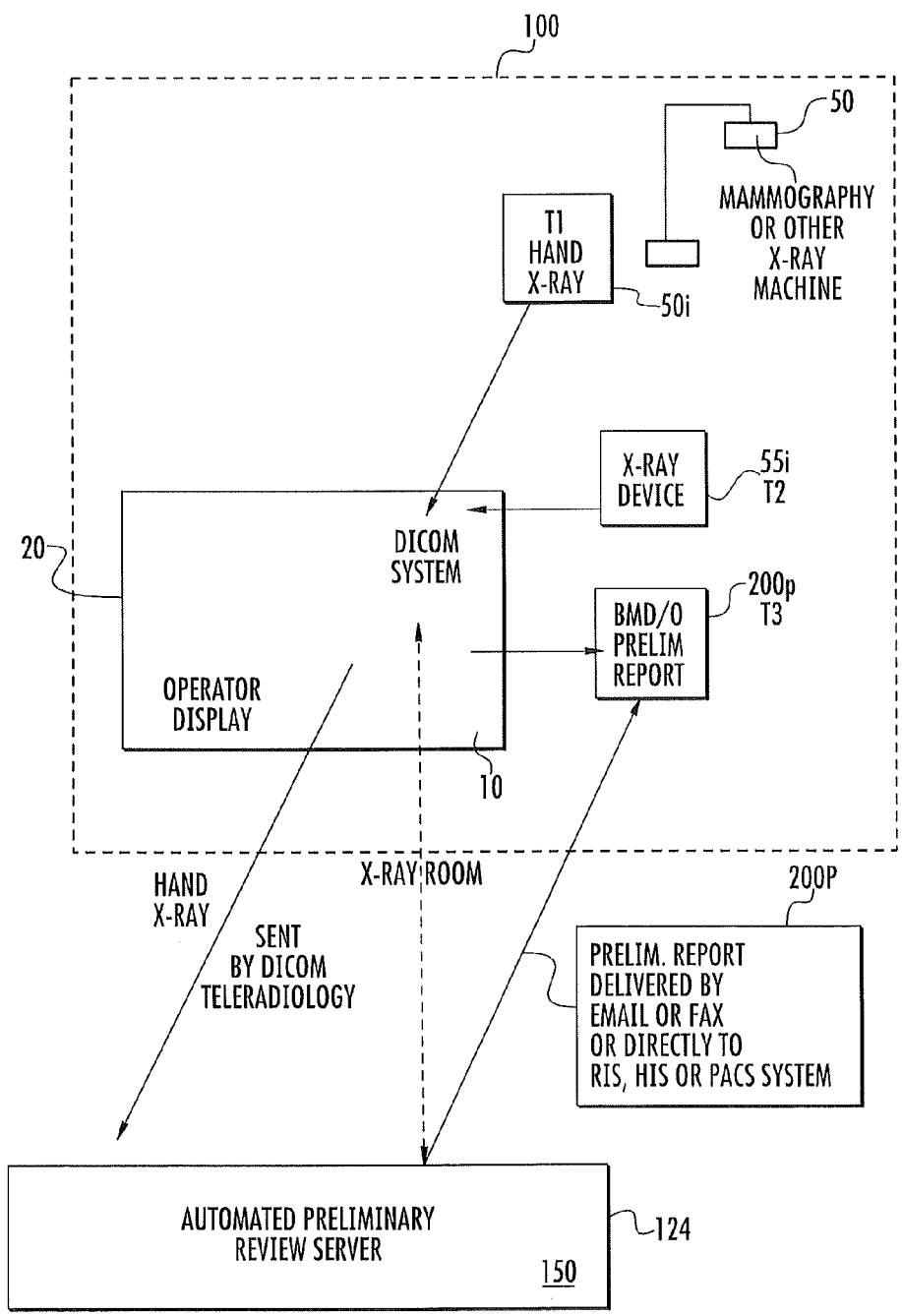
FIG. 5 is a schematic illustration of an X-ray site with a DICOM system in communication with an automated preliminary review server according to some embodiments of the present invention.

FIG. 5 is a schematic illustration of an X-ray site 100 with an efficient workflow according to some embodiments of the present invention. At time, T1, the hand X-ray 50*i* is obtained. This X-ray 50*i* is transmitted to the server 150 for rapid image analysis and generation of the preliminary report 200*p*. Mammography X-rays 55*i* are obtained after or during transmission of the hand X-ray 50*i* at time, T2. Before, or proximate in time to when the mammography X-rays have been acquired, the preliminary report 200*p* is received at the X-ray site 100, clinician site 300 or other designated site or location, at time T3. The total time for T1 to T2 can be between about 5-15 minutes. In some embodiments, the time frame for T1-T3 is less than the time to acquire the mammograms, e.g., T2. That is, the BMD/O automated review results with preliminary report 200*p* can be generated and transmitted back to the user while the mammography machine acquires the series of mammogram X-rays. In some embodiments, the rapid automated image analysis is carried out and the associated preliminary report 200*p* is transmitted back substantially instantaneously once the hand X-ray (and patient data, such as age or date of birth) is transmitted for analysis to the server 150 and in any event, such that the report 200*p* is provided before the patient exits the X-ray room or suite.

It is noted that while embodiments of the present invention use a remote server for the image analysis, it is contemplated that different clinic sites or each facility or room may have a dedicated on site image analysis circuit. The image analysis circuit may also be loaded directly onto selected workstations at the imaging site. Once the preliminary report is generated, the X-ray and patient data (with or without the preliminary report) is transmitted to the remote site for review by the remote expert.

The image analysis circuit or module 124 can be configured with any suitable image processing technique to evaluate the hand X-ray image.

The preliminary report 200*p* is typically generated if the measurement is made without residual errors and/or image miscalculation parameters that may unduly influence the validity of the measurement. In some embodiments, the image analysis module 124 is configured to evaluate whether the automated measurement is sufficiently reliable using a pre-defined risk threshold. The risk threshold can be set by evaluating certain defined characteristics of the image/image features to determine a likelihood that the report is at about at least a 90% confidence level, typically above 90%, as discussed with respect to the definition of the term "reliable", that the BMD measurement and/or osteoporosis evaluation is valid. The potential sources of risk include, for example, bone shape, grey scale transfer function, image resolution and the like. Thus, the risk threshold estimates how confident the computed automated rapid measurement is based on parameters assessed by the image analysis model.

The image analysis can be carried out to automatically evaluate the image for risk of fragility fractures for assessing osteoporosis. As shown in FIGS. 8A and 8B, the reports 200*p* (and 200*f*) include a BMD measurement, a T-score, a Z-score and a color-coded graph of the BMD measurement relative to defined norms of acceptable, marginal or bad (degrees of risk associated with the measurement). The acceptable range can be shown in green, the marginal in yellow and the "bad" in red, for example. The patient name, identification, date of birth and the like are optional and may or may not be provided as data fields on a respective report.

Figure 8C:
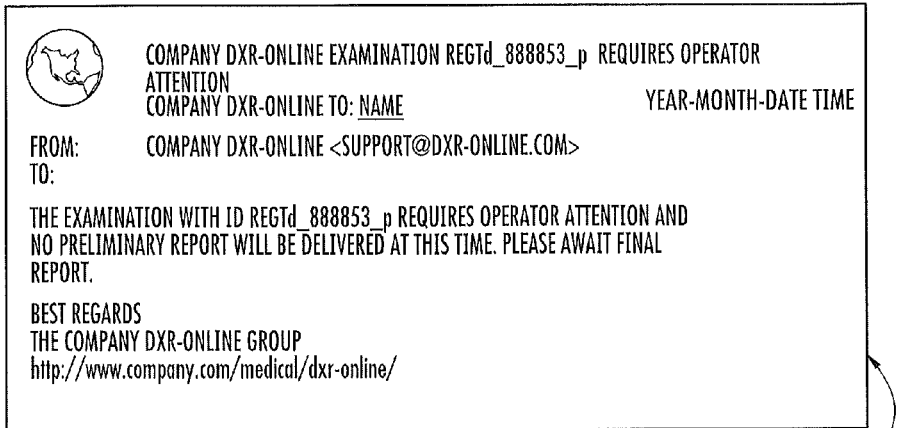
FIG. 8C is an example of a "no preliminary report" message that can be generated according to some embodiments of the present invention.

It is contemplated that only about 2 cases in 1000 preliminary reports with measurements will generate results that are subsequently declared invalid by an expert reviewer. Stated differently, in some embodiments, when the automated review sends the preliminary report with a BMD measurement, the evaluation will be over 99% reliable. It is also contemplated that for about 30 cases in 1000, no preliminary report with measurements or osteoporosis risk evaluation will be generated. Rather, a message or the report will just state "wait for final report" or "preliminary report not available" and the like, due to uncertainty identified in the automated evaluation. An example of this type of report or message 200*n* is shown in FIG. 8C.

After convergence, there will be a residual error that defines the difference between the trained model of normal metacarpal shapes and the converged location of shape points around the metacarpal edges in the image. The residual error may also be adjusted to account for other risk factors, such as the shape of the gray scale profile at the metacarpal bone edges perpendicular to the bone, the location of the converged model relative to other bone structures, atypical shape of one or more of the three metacarpal bones and the like.

Figure 6:
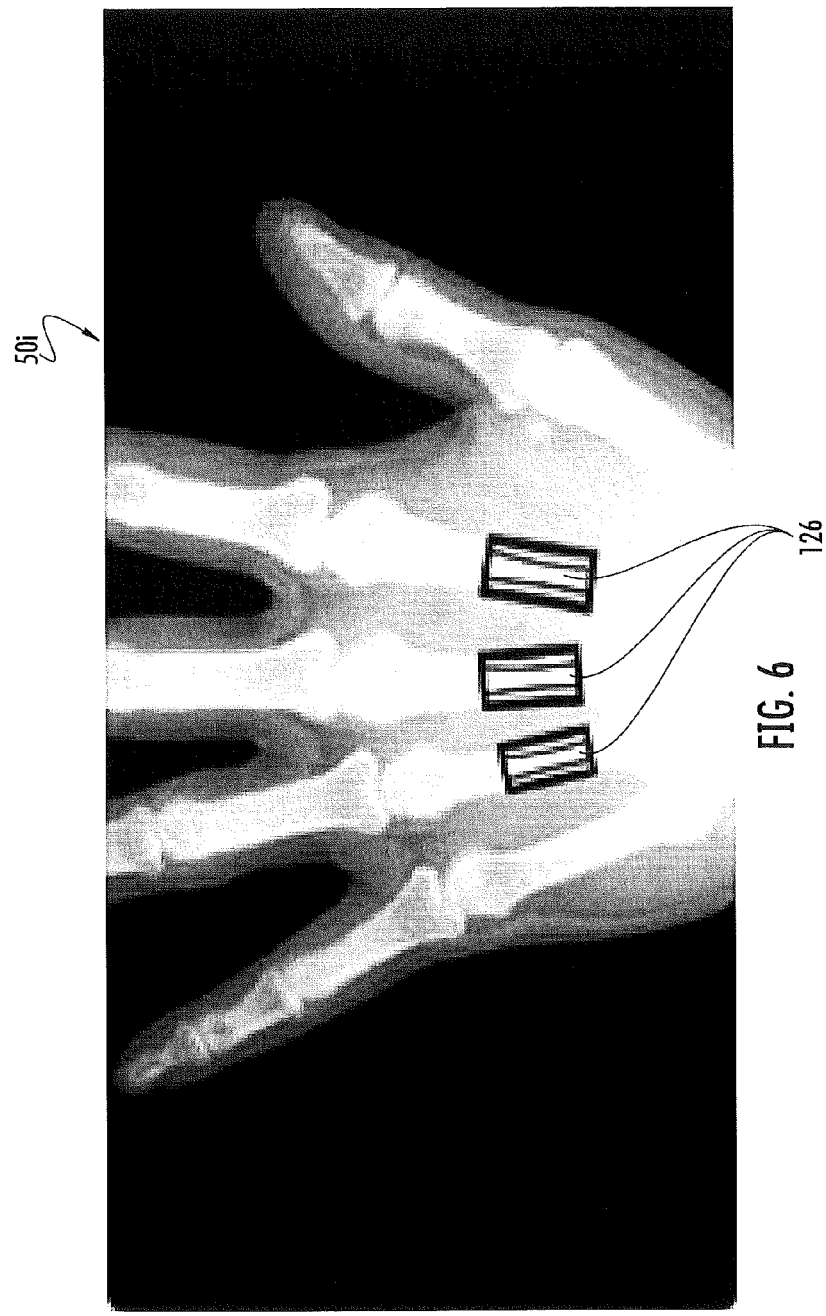
FIG. 6 is a digital image illustrating an example of an image processing analysis according to some embodiments of the present invention.

FIG. 6 illustrates a hand image 50*i* with a model 126 applied to three middle metacarpals, after convergence.

In some embodiments, the model 126 can comprise an active shape model (ASM) that can be applied to the three middle metacarpals. See, T. F. Cootes and C. J. Taylor and D. H. Cooper and J. Graham (1995). "Active shape models— their training and application." *Computer Vision and Image Understanding* (61): 38-59, the contents of which are hereby incorporated by reference herein.

In some embodiments, the residual error of the model can be expressed by Equation 1:

$$r = x - \bar{x} - \Phi b \quad \text{Equation 1}$$

and the square magnitude of the residual error can be expressed by:

$$|r|^2 = r^T r. \quad \text{Equation 2}$$

Other models may define residual errors in different manners. However, image analysis and preliminary report server 150 can be configured to determine whether to generate a risk report with measurements based on a pre-defined risk threshold. The risk threshold estimates how confident the measurement is based on parameters assessed by the model. In the ASM model, the parameters are for the residual error. If the residual error is lower than a predefined threshold, the server 150 and/or preliminary report module 124 can send out the automated preliminary report 200*p* to the user clinic, for example.

If the residual error from the model is larger than the predefined threshold, the message to the user clinic will instead state that the image requires operator review and that the final report must be awaited.

In some embodiments, Equation 3 can be used for the predefined risk threshold associated with a decision on whether to send a preliminary report with the BMD measurement(s) or not send the report (at least one with measurements):

$$r^T r < \text{constT}, \quad \text{Equation 3}$$

where constT is the predefined decision threshold.

Other image analysis technologies can be used to estimate the risk of a failed or unreliable analysis, including, for example, the residual error of an active appearance model (Edwards G, Taylor C, Cootes T. *Interpreting face images using active appearance models Proceeding of the International Conference on Face And Gesture Recognition*, 1998, pages 300-305); Residual error of a SIFT-based detection (Lowe, David G. (1999). "Object recognition from local scale-invariant features." Proceedings of the International Conference on Computer Vision. 2. pp. 1150-1157), and the like.

Figure 8D:
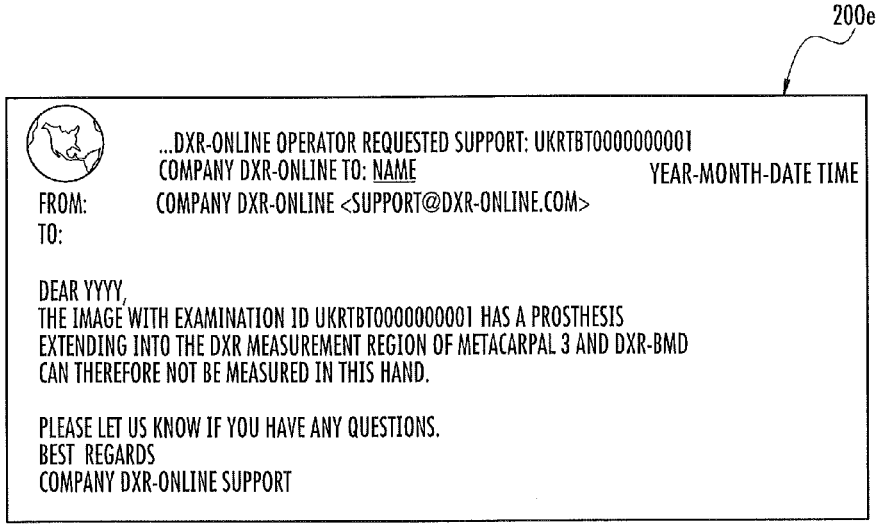
FIG. 8D is an example of a "failure message" that that be generated according to some embodiments of the present invention.

After the automated preliminary review, e.g. at a later time the same day or next few days, a trained human operator reviews the automated BMD analysis and sends a final report 200*f* or, in the case of rejection, a message to the clinic that no BMD measurement can be made and that the patient must be advised. An example of a failure message or report 200*e* is shown in FIG. 8D. In this example, the image was determined to have a prosthesis that extends into the DXR measurement region of metacarpal 3 such that DXR-BMD cannot be measured in this hand.

As noted above, it is expected that in approximately 30 cases in 1000, no preliminary report with BMD measurements will be delivered but instead a "wait for final report" message or a preliminary report with the message or other notice (but otherwise indicating no confident assessment or measurement was made) will be generated. It is expected that in approximately 2 cases in 1000, a preliminary report will be delivered but at the manual expert operator review, these 2 cases will be declared invalid. However, it is contemplated that in the vast majority of cases, no change will be made to the data in the BMD/O preliminary report 200*p* and the automated review with the preliminary report data will be validated as the final report 200*f*.

Figure 7:
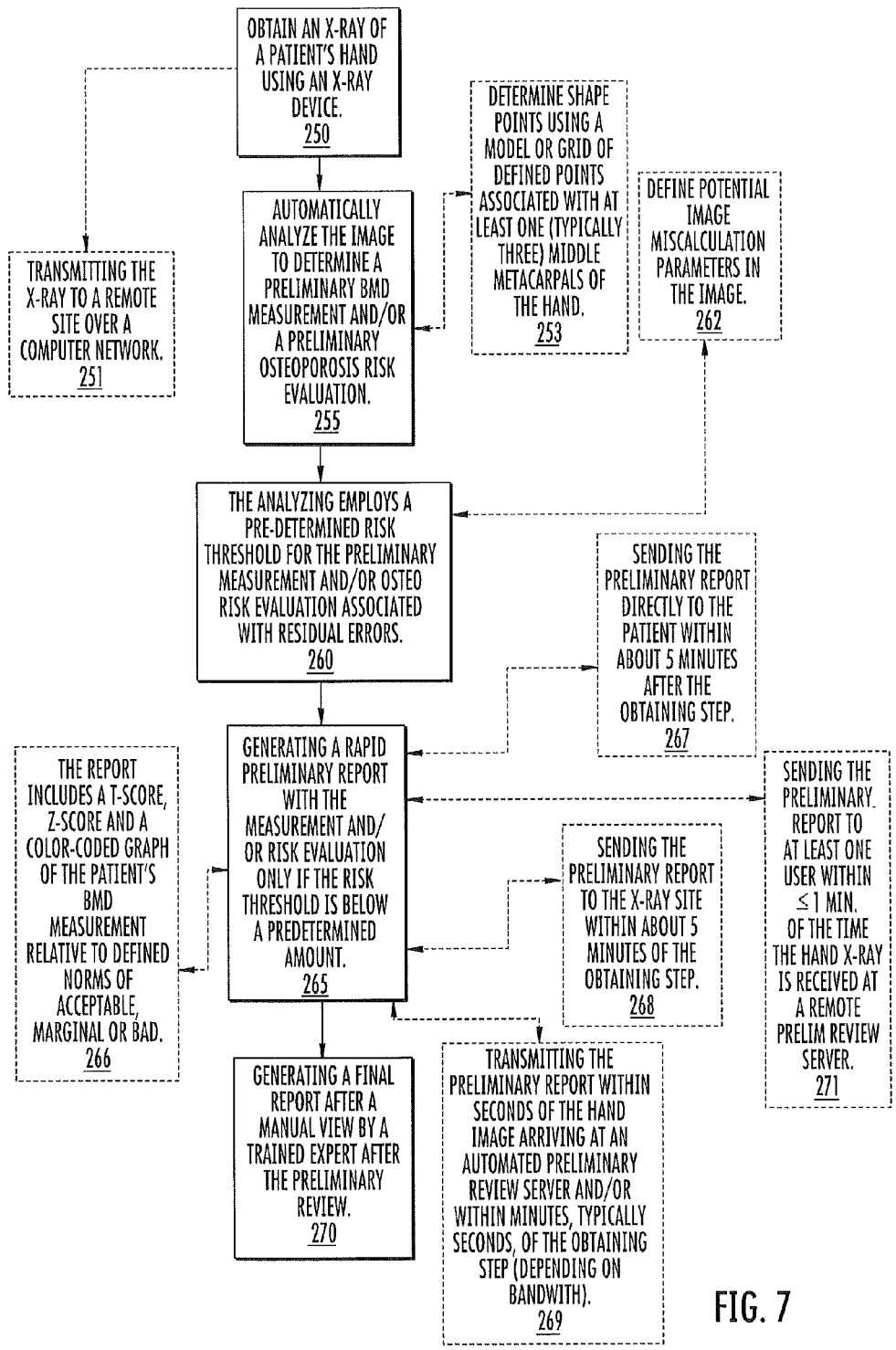
FIG. 7 is a flow chart of exemplary operations that can be used to carry out some embodiments of the present invention.

Turning now to FIG. 7, exemplary operations are shown which can be used to carry out embodiments of the present invention. An X-ray of a patient's hand is obtained using an X-ray (e.g., mammography) device (block 250). The image is automatically analyzed to determine a preliminary BMD measurement and/or a preliminary osteoporosis risk evaluation (block 255). The analyzing operation can employ a predetermined risk threshold for the preliminary measurement and/or osteoporosis risk evaluation associated with residual errors (block 260). A rapid preliminary report with the measurement and/or risk evaluation is generated (such that measurements are only included) if the risk threshold is below a predetermined amount (block 265). A final report is generated based on a manual view by a trained expert after the preliminary, review (block 270).

The method may include transmitting the X-ray to a remote site over a computer network (block 251).

The report can include one or more of a T-score, Z-score and a color-coded graph of the patient's BMD measurement relative to defined norms of acceptable, marginal or bad (block 266).

Shape points can be determined using a model or grid of defined points associated with three middle metacarpals of the hand (block 253).

Potential image miscalculation parameters in the image can be identified (block 262).

The preliminary report can be sent directly to the patient within about 5 minute after the X-ray is obtained (block 267). The preliminary report can be sent to the X-ray site and/or to a clinician within about 5 minutes of the acquisition of the X-ray (block 268).

The preliminary report can be sent to at least one user (clinician, radiology site, patient) within about 1 minute or less from a time of receipt of the hand X-ray at the preliminary review server (block 271).

In some embodiments, the preliminary report is transmitted within seconds of the hand image arriving at the automated preliminary review server and/or within minutes, typically seconds, from when the X-ray is obtained (depending on bandwidth) (block 269).

FIGS. 8A and 8B illustrate examples of the preliminary report 200p and the final report 200f. In this example, the BMD measurement, the Z-score and the T-score are the same in the preliminary and final reports 200p, 200f. An example of a preliminary report 200n that indicates no (reliable) measurement can be generated is shown in FIG. 8C. It is contemplated where there is a change in any of the noted measurements in the final report, then a header or other visually prominent notice may be appended to the final report 200f. As noted above, FIG. 8D is an example of a "failure" final report 200e from an expert site that can summarize why no BMD measurement can be generated.

As discussed above, embodiments of the present invention may take the form of an entirely software embodiment or an embodiment combining software and hardware aspects, all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices. Some circuits, modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller. Embodiments of the present invention are not limited to a particular programming language.

Computer program code for carrying out operations of data processing systems, method steps or actions, modules or circuits (or portions thereof) discussed herein may be written in a high-level programming language, such as Python, Java, AJAX (Asynchronous JavaScript), C, and/or C++, for development convenience. In addition, computer program code for carrying out operations of exemplary embodiments may also be written in other programming languages, such as, but not limited to, interpreted languages. Some modules or routines may be written in assembly language or even micro-code to enhance performance and/or memory usage. However, embodiments are not limited to a particular programming language. As noted above, the functionality of any or all of the program modules may also be implemented using discrete hardware components, one or more application specific integrated circuits (ASICs), or a programmed digital signal processor or microcontroller. The program code may execute entirely on one (e.g., a workstation computer), partly on one computer, as a stand-alone software package, partly on the workstation's computer or Scanner's computer and partly on another computer, local and/or remote or entirely on the other local or remote computer. In the latter scenario, the other local or remote computer may be connected to the user's computer through a local area network (LAN) or a wide area network (WAN), or the connection may be made to an external computer (for example, through the Internet using an Internet Service Provider).

The present invention is described in part with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing some or all of the functions/acts specified in the flowchart and/or block diagram block or blocks.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order or two or more blocks may be combined, depending upon the functionality involved.

Figure 9:
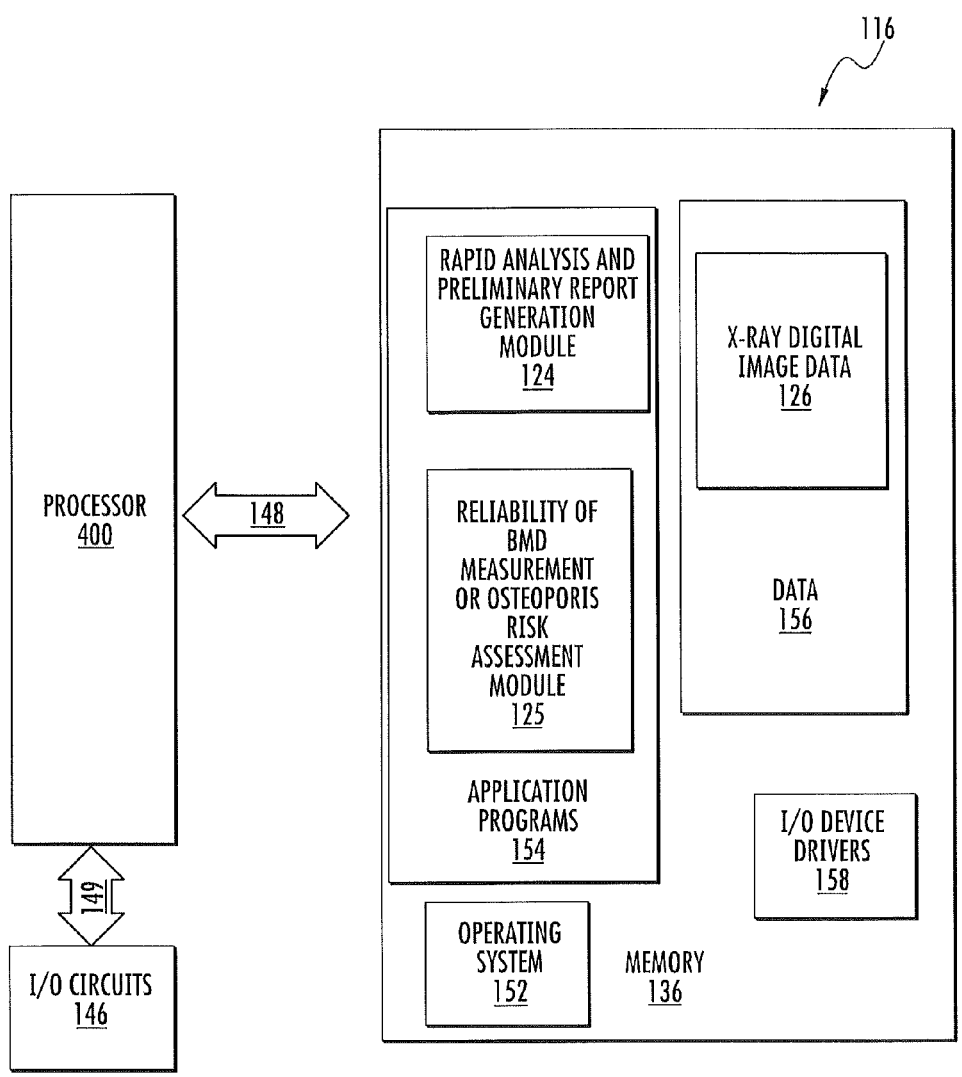
FIG. 9 is a schematic illustration of a data processing circuit or system according to some embodiments of the present invention.

As illustrated in FIG. 9, embodiments of the invention may be configured as a data processing system 116, which can be used to carry out or direct operations of the rendering, and can include a processor circuit 400, a memory 136 and input/output circuits 146. The data processing system may be incorporated in, for example, one or more of a personal computer, workstation 10w, server, router or the like. The system 116 can reside on one machine or be distributed over a plurality of machines. The processor 400 communicates with the memory 136 via an address/data bus 148 and communicates with the input/output circuits 146 via an address/data bus 149. The input/output circuits 146 can be used to transfer information between the memory (memory and/or storage media) 136 and another computer system or a network using, for example, an Internet protocol (IP) connection. These components may be conventional components such as those used in many conventional data processing systems, which may be configured to operate as described herein.

In particular, the processor 400 can be commercially available or custom microprocessor, microcontroller, digital signal processor or the like. The memory 136 may include any memory devices and/or storage media containing the software and data used to implement the functionality circuits or modules used in accordance with embodiments of the present invention. The memory 136 can include, but is not limited to, the following types of devices: ROM, PROM, EPROM, EEPROM, flash memory, SRAM, DRAM and magnetic disk. In some embodiments of the present invention, the memory 136 may be a content addressable memory (CAM).

As further illustrated in FIG. 9, the memory (and/or storage media) 136 may include several categories of software and data used in the data processing system: an operating system 152; application programs 154; input/output device drivers 158; and data 156. As will be appreciated by those of skill in the art, the operating system 152 may be any operating system suitable for use with a data processing system, such as IBM®, OS/2®, AIX® or zOS® operating systems or Microsoft® Windows®95, Windows98, Windows2000or WindowsXP operating systems Unix or Linux™. IBM, OS/2, AIX and zOS are trademarks of International Business Machines Corporation in the United States, other countries, or both while Linux is a trademark of Linus Torvalds in the United States, other countries, or both. Microsoft and Windows are trademarks of Microsoft Corporation in the United States, other countries, or both. The input/output device drivers 158 typically include software routines accessed through the operating system 152 by the application programs 154 to communicate with devices such as the input/output circuits 146 and certain memory 136 components. The application programs 154 are illustrative of the programs that implement the various features of the circuits and modules according to some embodiments of the present invention. Finally, the data 156 represents the static and dynamic data used by the application programs 154 the operating system 152 the input/output device drivers 158 and other software programs that may reside in the memory 136.

The data 156 may include (archived or stored) digital image data sets 126 correlated to respective patients. As further illustrated in FIG. 9, according to some embodiments of the present invention application programs 154 include a Rapid Analysis and Preliminary Report Generation Module 124 and a Reliability of BMD Measurement or Osteoporosis Risk Assessment Module 125. The data interface module can be decoupled or isolated from the visualization/rendering module. The application program 154 may be located in a local server (or processor) and/or database or a remote server (or processor) and/or database, or combinations of local and remote databases and/or servers.

While the present invention is illustrated with reference to the application programs 154, and Modules 124, 125 in FIG. 9, as will be appreciated by those of skill in the art, other configurations fall within the scope of the present invention. For example, rather than being application programs 154 these circuits and modules may also be incorporated into the operating system 152 or other such logical division of the data processing system. Furthermore, while the application programs 124, 125 are illustrated in a single data processing system, as will be appreciated by those of skill in the art, such functionality may be distributed across one or more data processing systems in, for example, the type of client/server arrangement described above. Thus, the present invention should not be construed as limited to the configurations illustrated in FIG. 9 but may be provided by other arrangements and/or divisions of functions between data processing systems. For example, although FIG. 9 is illustrated as having various circuits and modules, one or more of these circuits or modules may be combined or separated without departing from the scope of the present invention.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A rapid analysis and preliminary reporting system for evaluating bone mineral density (BMD) for assessing a patient's risk of osteoporosis, comprising:

a plurality of different radiology sites, each having at least one radiology workstation in communication with a display and at least one X-ray device in communication with the at least one radiology workstation;

a preliminary BMD report circuit in communication with the different radiology sites via the Internet, the preliminary BMD report circuit comprising an automated rapid image analysis module configured to receive and analyze hand X-rays taken from respective X-ray devices using an image analysis model that is applied to at least one middle metacarpal finger in a respective hand X-ray undergoing analysis, wherein the preliminary BMD report circuit is configured to carry out the analysis, generate a preliminary BMD report comprising an associated BMD measurement with an osteoporosis risk report and transmit the preliminary BMD report to at least one user substantially instantaneously upon receipt of a respective hand X-ray from a radiology site and/or an associated radiology workstation or X-ray device; and at least one remote expert site with at least one expert workstation in communication with the preliminary BMD report circuit and/or radiology workstations, wherein the preliminary BMD report circuit is also configured to provide the preliminary BMD reports with associated hand X-rays to one or more of the at least one expert workstation to allow a BMD image analysis expert to review respective hand X-rays and associated preliminary BMD reports of different patients from different radiology sites and decide whether to validate or invalidate data reported in respective preliminary BMD reports, wherein the preliminary BMD report circuit or the at least one remote expert workstation is configured to transmit respective final BMD reports to radiology sites and/or defined users after the BMD image analysis expert validates or invalidates the related preliminary BMD report, wherein the preliminary BMD report circuit or the at least one remote expert workstation is configured to generate and transmit each of the following for each preliminary BMD report, depending on an expert's review thereof at the at least one expert workstation: (i) the final BMD report of osteoporosis risk with the BMD measurement from the preliminary BMD report; or (ii) the final BMD report indicating a corresponding preliminary BMD report with the BMD measurement is invalid, wherein the preliminary BMD reports are transmitted to the at least one user associated with a corresponding radiology site and/or patient within about 5 minutes from receipt of a respective hand X-ray from respective radiology workstations or X-ray devices at the different radiology sites, and wherein the preliminary BMD report circuit is configured to electronically determine whether there are residual errors and/or irregular image features to calculate a risk threshold for establishing whether the BMD measurement of the respective preliminary BMD reports is reliable, and wherein the preliminary report circuit is configured to (i) transmit the preliminary BMD reports with a corresponding BMD measurement to patients and/or users associated with a radiology site only if the corresponding BMD measurement is determined to be reliable and (ii) provide preliminary BMD reports with the corresponding BMD measurement to one or more of the at least one expert workstation irrespective of whether the BMD measurement is considered reliable.

2. The system of claim 1, wherein the preliminary BMD report transmitted to the at least one user comprises a header with text adjacent "report" with one or more words that identifies the preliminary BMD report as preliminary, and wherein the final BMD report comprises text with one or more words that identifies the final BMD report as final.

3. The system of claim 1, wherein the preliminary BMD report circuit is held at least partially in a remote server, and wherein respective radiology workstations transmit hand X-ray images in DICOM format to the remote server via the Internet.

4. The system of claim 1, wherein the preliminary BMD report circuit is configured to carry out the analysis, generate and transmit the preliminary BMD reports to the at least one user within about 30 seconds from receipt of a respective hand X-ray from respective radiology workstations or X-ray devices at the different radiology sites.

5. The system of claim 1, wherein the preliminary BMD report comprises text with "preliminary" as a word thereof to provide a patient a visual indication of a preliminary status of the preliminary BMD report.

6. The system of claim 1, wherein the final BMD report comprises text with "final" as a word thereof to provide a patient a visual indication of an expert reviewed status of the final BMD report.

7. A rapid analysis and preliminary reporting system for evaluating bone mineral density (BMD) for assessing a patient's risk of osteoporosis, comprising:
a plurality of different radiology sites, each having at least one radiology workstation in communication with a display and at least one X-ray device in communication with the at least one radiology workstation:
a preliminary BMD report circuit in communication with the different radiology sites via the Internet, the preliminary BMD report circuit comprising an automated rapid image analysis module configured to receive and analyze hand X-rays taken from respective X-ray devices using an image analysis model that is applied to at least one middle metacarpal finger in a respective hand X-ray undergoing analysis, wherein the preliminary BMD report circuit is configured to carry out the analysis, generate a preliminary BMD report comprising an associated BMD measurement with an osteoporosis risk report and transmit the preliminary BMD report to at least one user substantially instantaneously upon receipt of a respective hand X-ray from a radiology site and/or an associated radiology workstation or X-ray device:, and at least one remote expert site with at least one expert workstation in communication with the preliminary BMD report circuit and/or radiology workstations, wherein the preliminary BMD report circuit is also configured to provide the preliminary BMD reports with associated hand X-rays to one or more of the at least one expert workstation to allow a BMD image analysis expert to review respective hand X-rays and associated preliminary BMD reports of different patients from different radiology sites and decide whether to validate or invalidate data reported in respective preliminary BMD reports, wherein the preliminary BMD report circuit or the at least one remote expert workstation is configured to transmit respective final BMD reports to radiology sites and/or defined users after the BMD image analysis expert validates or invalidates the related preliminary BMD report, wherein the preliminary BMD report circuit or the at least one remote expert workstation is configured to generate and transmit each of the following for each preliminary BMD report, depending on an expert's review thereof at the at least one expert workstation: i) the final BMD report of osteoporosis risk with the BMD measurement from the preliminary BMD report; or (ii) the final BMD report indicatin a corresponding preliminary BMD report with the BMD measurement is invalid, wherein the preliminary BMD reports are transmitted to the at least one user associated with a corresponding radiology site and/or patient within about 5 minutes from receipt of a respective hand X-ray from respective radiology workstations or X-ray devices at the different radiology sites, and wherein the preliminary BMD report circuit is configured to electronically determine whether the BMD measurement for each hand X-ray is reliable, and wherein the preliminary BMD report circuit is configured to (i) transmit the preliminary BMD reports of different patients with a corresponding hand X-ray and calculated BMD measurement to the at least one expert site with the at least one expert workstation for validation review and also (ii) selectively transmit preliminary BMD reports with the calculated BMD measurement only to patients and/or users at the different radiology sites if the BMD measurement therein is determined to be reliable.

8. The system of claim 7, wherein, if the corresponding BMD measurement of the preliminary BMD report is considered unreliable, the preliminary BMD report circuit is configured to carry out both (i) and (ii) but (ii) is carried out to transmit the preliminary BMD report to at least one user associated with a respective radiology site without a BMD measurement.

9. The system of claim 8, wherein the preliminary BMD report includes a header with text with one or more words that identifies the report as preliminary, and wherein the preliminary BMD report includes an image of the patient's hand-X-ray, a color-coded graph with a patient's BMD measurement, a T-score and a Z-score.

10. A rapid analysis and preliminary reporting system for evaluating bone mineral density (BMD) for assessing a patient's risk of osteoporosis, comprising:
   a preliminary BMD report circuit comprising at least one server in communication with a plurality of radiology sites using the internet; and
   at least one remote expert site with at least one expert workstation in communication with the preliminary BMD report circuit,
   wherein the preliminary BMD report circuit comprises an automated rapid image analysis module configured to analyze respective hand X-rays from the plurality of radiology sites, wherein the automated rapid image analysis module is configured to apply an image analysis model to at least one middle metacarpal finger in a respective hand X-ray undergoing analysis, wherein the preliminary BMD report circuit is configured to then electronically transmit a preliminary BMD report of osteoporosis risk back to a respective radiology site and/or to at least one defined user associated with a radiology site or a patient corresponding to the hand X-ray undergoing analysis substantially instantaneously so that the preliminary BMD reports are received at respective radiology sites, other defined sites and/or by defined users within about two minutes from receipt from a radiology site of a respective hand X-ray at the at least one server of the preliminary BMD report circuit, wherein the preliminary BMD report circuit is configured to selectively transmit preliminary BMD reports so that the preliminary BMD reports that include a calculated BMD measurement are only provided to patients and/or users at the different radiology sites if the BMD measurement associated therewith is determined to be reliable by the preliminary BMD report circuit, otherwise a BMD preliminary report or message is provided that indicates a preliminary BMD analysis is not available and a BMD measurement is pending a BMD image analysis expert review,
   wherein a respective expert workstation is configured to allow a BMD image analysis expert to review preliminary BMD reports comprising a calculated BMD measurement and corresponding hand X-ray of different patients from different radiology sites and decide whether to validate or invalidate data reported in respective preliminary BMD reports with calculated BMD measurements, and wherein the at least one server and/or the at least one expert workstation is configured to directly or indirectly generate and transmit final BMD reports to respective radiology sites and/or to defined users after the expert validates or invalidates the reported data, and wherein, when the BMD measurement in the preliminary report is determined to be reliable by the preliminary BMD report circuit, the preliminary report and the final report are provided as duplicate reports except for different report headers and both the preliminary report and the final report include a patient's BMD measurement, a T-score and a Z-score, and the final BMD report presents each of the BMD measurement, the T-score and the Z-score unchanged from the preliminary report.

11. The system of claim 10, wherein the preliminary BMD reports comprise a header that includes the word "preliminary" to visually mark the preliminary BMD reports as preliminary, and wherein the final BMD reports comprise a header that includes the word "final" to visually mark the final BMD reports as final.

12. The system of claim 11, wherein the text of the preliminary BMD reports comprises the word "report" adjacent the word "preliminary" to provide a patient a visual indication of a preliminary status of a respective preliminary BMD report, and wherein the text of the final BMD reports comprises the word "report" adjacent the word "final" to provide a patient a visual indication of an expert reviewed status of a respective final BMD report, and wherein the preliminary report and the final report both also include an image of the patient's hand-X-ray and a color-coded graph with the patient's BMD measurement.

* * * * *